(12) United States Patent
Baba et al.

(10) Patent No.: US 7,869,049 B2
(45) Date of Patent: Jan. 11, 2011

(54) DETERMINING BIOLOGICAL TISSUE OPTICAL PROPERTIES VIA INTEGRATING SPHERE SPATIAL MEASUREMENTS

(75) Inventors: Justin S. Baba, Knoxville, TN (US); Brian S. Letzen, Coral Springs, FL (US)

(73) Assignee: UT-Battelle, LLC, Oak Ridge, TN (US)

( * ) Notice: Subject to any disclaimer, the term of this patent is extended or adjusted under 35 U.S.C. 154(b) by 90 days.

(21) Appl. No.: 12/436,329

(22) Filed: May 6, 2009

(65) Prior Publication Data

US 2010/0284014 A1 Nov. 11, 2010

(51) Int. Cl.
*G01N 21/47* (2006.01)
*G01B 9/02* (2006.01)
(52) U.S. Cl. .................. 356/446; 356/451
(58) Field of Classification Search .......... 356/446, 356/451
See application file for complete search history.

(56) References Cited

U.S. PATENT DOCUMENTS

| | | | | |
|---|---|---|---|---|
| 4,752,689 | A * | 6/1988 | Satake | 250/339.07 |
| 4,932,779 | A * | 6/1990 | Keane | 356/319 |
| 5,630,423 | A | 5/1997 | Wang et al. | |
| 5,636,015 | A | 6/1997 | Imura et al. | |
| 5,745,234 | A | 4/1998 | Snail et al. | |
| 6,088,117 | A * | 7/2000 | Imura et al. | 356/445 |
| 6,632,401 | B1 * | 10/2003 | Wulf | 422/82.08 |

OTHER PUBLICATIONS

Coquoz et al., "Optical properly measurements of turbid media in a small-volume cuvette with frequency-domain photon migration", Applied Optics, Dec. 1, 2001, pp. 6281-6291, vol. 40, No. 34.
Lin et al., "Measurement of tissue optical properties by the use of oblique-incidence optical fiber reflectometry", Applied Optics, Jan. 1, 1997, pp. 136-143, vol. 36, No. 1.
Marquez et al., "White light oblique incidence reflectometer for measuring absorption and reduced scattering spectra of tissue-like turbid media", Optics Express, Dec. 22, 1997, pp. 454-460, vol. 1, No. 13.
Pickering et al., "Double-integrating-sphere system for measuring the optical properties of tissue", Applied Optics, Feb. 1, 1993, pp. 399-410, vol. 32, No. 4.

(Continued)

*Primary Examiner*—Roy Punnoose
(74) *Attorney, Agent, or Firm*—Scully, Scott, Murphy & Presser, P.C (57) ABSTRACT

An optical sample is mounted on a spatial-acquisition apparatus that is placed in or on an enclosure. An incident beam is irradiated on a surface of the sample and the specular reflection is allowed to escape from the enclosure through an opening. The spatial-acquisition apparatus is provided with a light-occluding slider that moves in front of the sample to block portions of diffuse scattering from the sample. As the light-occluding slider moves across the front of the sample, diffuse light scattered into the area of the backside of the light-occluding slider is absorbed by back side surface of the light-occluding slider. By measuring a baseline diffuse reflectance without a light-occluding slider and subtracting measured diffuse reflectance with a light-occluding slider therefrom, diffuse reflectance for the area blocked by the light-occluding slider can be calculated.

36 Claims, 6 Drawing Sheets

OTHER PUBLICATIONS

Prahl et al., "Determining the optical properties of turbid media by using the adding-doubling method", Applied Optics, Feb. 1, 1993, pp. 559-568, vol. 32, No. 4.

Prerana et al., "Method to determine the optical properties of turbid media", Applied Optics, Jun. 10, 2008, pp. 3216-3220, vol. 47, No. 17.

Takagi et al., "Alternative Oblique-Incidence Reflectometry for Measuring Tissue Optical Properties", Optical Review, 2000, pp. 164-169, vol. 7, No. 2.

Wang et al., "Use of a laser beam with an oblique angle of incidence to measure the reduced scattering coefficient of a turbid medium", Applied Optics, May 1, 1995, pp. 2362-2366, vol. 34, No. 13.

* cited by examiner

DETERMINING BIOLOGICAL TISSUE OPTICAL PROPERTIES VIA INTEGRATING SPHERE SPATIAL MEASUREMENTS

STATEMENT REGARDING FEDERALLY SPONSORED RESEARCH OR DEVELOPMENT

This invention was made with United States government support under Prime Contract No. DE-AC05-00OR22725 awarded by the U.S. Department of Energy. The United States government has certain rights in this invention.

FIELD OF THE INVENTION

The present invention relates to the field of optical measurement, and specifically to an optical apparatus, a method of operating the same, and a program to perform the operation of the same.

BACKGROUND OF THE INVENTION

Biomedical optics is an emerging field with enormous potential to diagnose and treat diseases safely and economically. Success in application of biomedical optics is highly dependent on accurate characterization of optical properties of target tissues. Particularly, the interaction of a particular type of tissue with light needs thorough and accurate characterization to predict the interaction of light with such a tissue during treatment.

Integrating spheres provide a wealth of benefits, such as isotropic detection of reflectance from samples that reflect light and the ability to accurately measure even the lowest light intensities that are otherwise impossible to measure with other optical measuring techniques. The inherent symmetry of the integrating sphere provides an accurate means of measuring light intensity by diffusely distributing all light intensity evenly within its inner cavity. However, this advantage also comes with the disadvantage of destroying all spatial information from a sample. As such, there is currently no way of determining spatial data within an integrating sphere.

Further, the integrating sphere currently available suffers from a few limitations. The current industry-standard method for determining the optical properties of tissue involves taking both a transmittance and reflectance measurement to determine the absorption and scattering of light in the tissue. An extremely thin slice of tissue, typically thin enough to allow enough transmission of light through the thin slice, is necessary for such transmittance measurements. Preparation of such thin slices of tissue can be effected by using of a microtome device that appropriately slices a frozen tissue. However, the process of microtome takes time and expense. In addition, freezing of a sample tissue sample to enable microtome slicing introduces physically changes to the structure of the sample itself. As a consequence, the measured optical properties of a sample prepared by microtome can deviate from the true optical properties of an undamaged sample by the artifacts of the structural damage introduced into the prepared sample due to the freezing and the mechanical slicing.

In addition, the prior art method for determining optical properties within an integrating sphere requires manually moving the sample to different port positions in order to obtain both reflectance and transmission measurements. Since it is extremely difficult for the user to manually position the sample perfectly by visual inspection alone, the data collected represents an inconsistent measurement of the sample. A double-integrating sphere approach has been proposed in an attempt to solve this problem, in which the sample is placed in the rear of the first sphere which becomes the front of a second adjacent integrating sphere. Besides the high cost of having to purchase a second integrating sphere, this prior art technique is limited to extremely thin tissue samples, since light must be transmitted into the second integrating sphere for measurement.

Due to the lack of an accurate and economic method for determining optical properties within a standard integrating sphere optical measurement device, translation of optical biomedical devices and technologies from research laboratories to clinics have been hampered. Thus, there exists a need for standardized optical property measurement that provides accurate characterization of a sample without having to perform microtome slicing.

SUMMARY OF THE INVENTION

In the present invention, an optical sample is mounted on a spatial-acquisition apparatus that is placed in or on an enclosure. An incident beam is irradiated on a surface of the sample and the specular reflection is allowed to escape from the enclosure through an opening. The spatial-acquisition apparatus is provided with a light-occluding slider that moves in front of the sample to block portions of diffuse re-emittance from the sample. The light after diffusely scattering in the sample is re-emitted and then reflected within the enclosure, lined with reflective surfaces, and is detected by a spectrophotometer. As the light-occluding slider moves across the front of the sample, diffuse light scattered into the area of the backside of the light-occluding slider is absorbed/blocked by back side surface of the light-occluding slider. By measuring a baseline diffuse reflectance without a light-occluding slider and subtracting measured diffuse reflectance with a light-occluding slider therefrom, diffuse reflectance for the area blocked by the light-occluding slider can be calculated. The diffuse reflectance per area as a function of the location of the light-occluding slider can be employed to determine the absorption coefficient and the scattering coefficient of the sample.

The optical properties of tissue are determined by collecting spatial reflectance data from a biological tissue using an integrating sphere. An automated positional light-occlusion apparatus is employed to provide a spatial measure of reflectance. The apparatus can be controlled by an automated program to receive and manipulate raw reflectance data, and convert this data to the optical properties of a sample using oblique-incidence theory. Positional information can be measured using an integrating sphere. The optical properties of biological tissue is readily determined by using an integrating sphere, accurately and economically, by an automated method.

According to an aspect of the present invention, an optical apparatus is provided, which includes: an enclosure having a reflective inner surface; a spatial-acquisition apparatus configured to hold a sample on a front side, wherein the front side is exposed to an interior of the enclosure; a light source configured to illuminate a collimated incident light beam onto a front surface of the sample; and a light-occluding slider covering a portion of the front side of the spatial-acquisition apparatus and configured to slide over the front side of the spatial-acquisition apparatus, wherein the light-occluding slider blocks a portion of diffuse scattered light from the sample upon irradiation with the collimated incident light.

In one embodiment, the optical apparatus further includes a spectrophotometer configured to detect an unblocked portion of the diffuse scattered light, and wherein the reflective inner surface extends across an entire inner surface of the enclosure.

In another embodiment, the optical apparatus further includes at least one linear actuator that is configured to move linearly, wherein the light-occluding slide is attached to the at least one linear actuator.

In even another embodiment, the optical apparatus further includes a controller configured to control movement of the at least one linear actuator and the light-occluding slider.

In yet another embodiment, the optical apparatus further includes a data acquisition apparatus configured to record at least one pair of first data and second data, wherein the first data describes a location of the light-occluding slider and the second data describes measured intensity of the unblocked portion of the diffuse scattered light as measured by the spectrometer when the light-occluding slider is at the location.

In still another embodiment, the optical apparatus further includes a computer configured to receive data from the data acquisition apparatus and to record a plurality of pairs of the first data and the second data corresponding to different locations of the light-occluding slider during a linear movement.

In a further embodiment, the computer is configured to calculate diffuse reflectance for each area blocked by the light-occluding slider based on the plurality of pairs of the first data and the second data.

According to another aspect of the present invention, a method of operating an optical apparatus is provided, which includes: providing an optical apparatus with an enclosure having a reflective inner surface and a spatial-acquisition apparatus; loading a sample on a front side of the spatial-acquisition apparatus; illuminating a collimated incident light beam onto a front surface of the sample; moving a light-occluding slider over the front surface of the sample, wherein the light-occluding slider blocks a portion of diffuse scattered light from the sample upon irradiation with the collimated incident light; and detecting an unblocked portion of the diffuse scattered light employing a spectrophotometer attached to an inside of the enclosure for at least one location of the light-occluding slider.

In one embodiment, the unblocked portion of the diffuse scattered light is detected for a plurality of locations of the light-occluding slider.

In another embodiment, the method further includes linearly moving at least one linear actuator by a signal from a controller, wherein the at least one linear actuator moves with the light-occluding slider.

In yet another embodiment, the method further includes collecting at least one pair of first data and second data employing a data acquisition apparatus, wherein the first data describes a location of the light-occluding slider and the second data describes measured intensity of the unblocked portion of the diffuse scattered light as measured by the spectrometer when the light-occluding slider is at the location.

In still another embodiment, the method further includes operating a computer configured to receive data from the data acquisition apparatus and to record a plurality of pairs of the first data and the second data corresponding to different locations of the light-occluding slider during a linear movement.

According to yet another aspect of the present invention, a machine-readable data storage device embodying a program of machine-executable instructions to perform a method of operating an optical apparatus is provided. The optical apparatus includes: a spatial-acquisition apparatus configured to hold a sample on a front side; a light source configured to illuminate a collimated incident light beam onto a front surface of the sample; and a light-occluding slider covering a portion of the front side of the spatial-acquisition apparatus, wherein the light-occluding slider blocks a portion of diffuse scattered light from the sample upon irradiation with the collimated incident light. The method includes: moving a light-occluding slider over a front surface of the sample while a collimated incident light beam is illuminated onto a front surface of the sample, wherein the light-occluding slider blocks a portion of diffuse scattered light from the sample upon irradiation with the collimated incident light; and detecting an unblocked portion of the diffuse scattered light employing a spectrophotometer for at least one location of the light-occluding slider.

In one embodiment, the optical apparatus further includes an enclosure having a reflective inner surface, wherein the front side of the spatial-acquisition apparatus is exposed to an interior of the enclosure.

In another embodiment, the method further includes detecting the unblocked portion of the diffuse scattered light for a plurality of locations of the light-occluding slider.

In even another embodiment, the method further includes linearly moving at least one linear actuator by a signal from a controller, wherein the at least one linear actuator moves with the light-occluding slider.

In still another embodiment, the method further includes operating a computer configured to receive data from the data acquisition apparatus and to record a plurality of pairs of the first data and the second data corresponding to different locations of the light-occluding slider during a linear movement.

In a further embodiment, the program of machine-executable instructions causes a linear movement of the light-occluding slider and triggers a measurement by the spectrophotometer and further causes the plurality of pairs of the first data and the second data to be automatically collected for each corresponding location of the light-occluding slider.

BRIEF DESCRIPTION OF THE DRAWINGS

It is noted that proportions of various elements in the accompanying figures are not drawn to scale to enable clear illustration of elements having smaller dimensions relative to other elements having larger dimensions.

DETAILED DESCRIPTION OF THE INVENTION

As stated above, the present invention relates to an optical apparatus, a method of operating the same, and a program to perform the operation of the same. The present invention is now described in detail with accompanying figures. It is noted that like and corresponding elements mentioned herein and illustrated in the drawings are referred to by like reference numerals.

Figure 1:
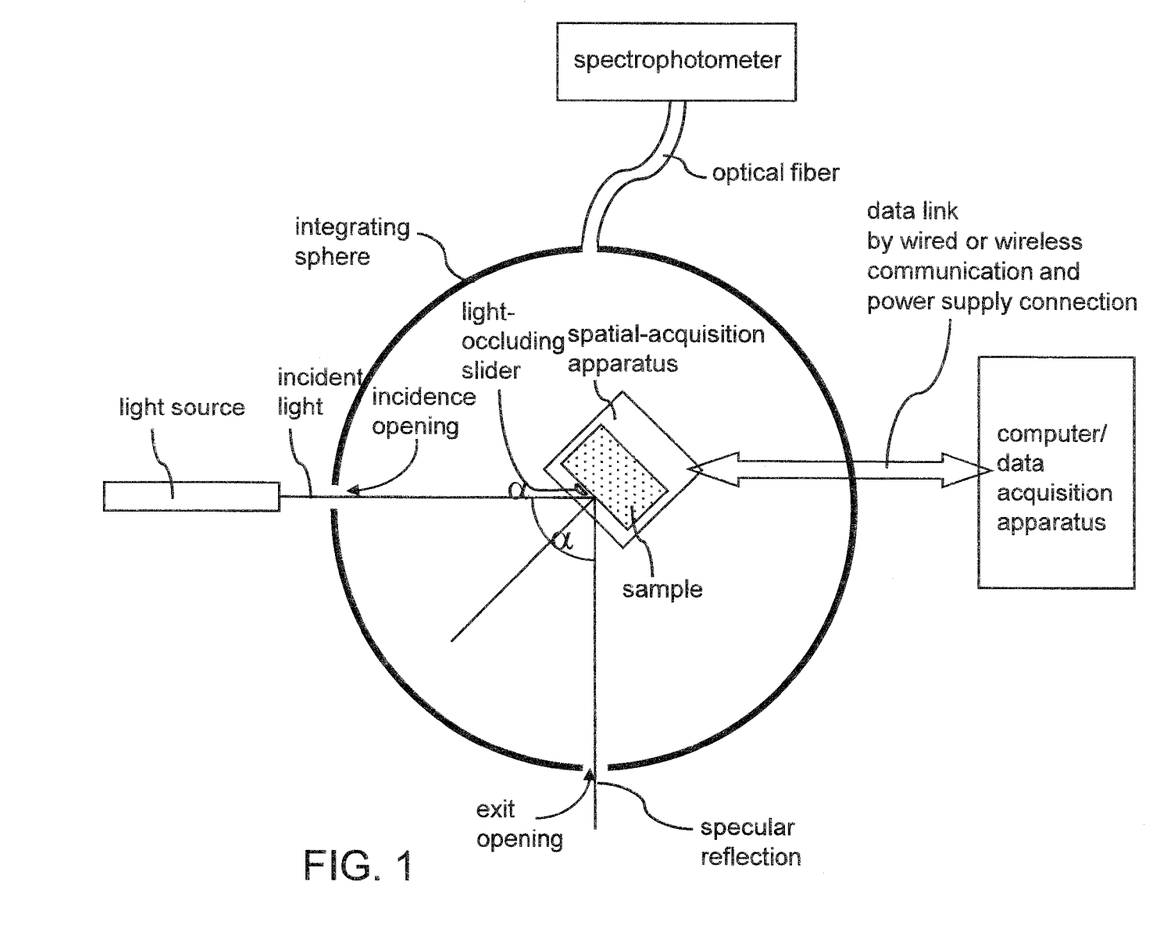
FIG. 1 is a schematic horizontal cross-sectional view of a first exemplary optical apparatus including a spatial-acquisition apparatus located in an optical integrating sphere and a spectrophotometer of the present invention.
Figure 2:
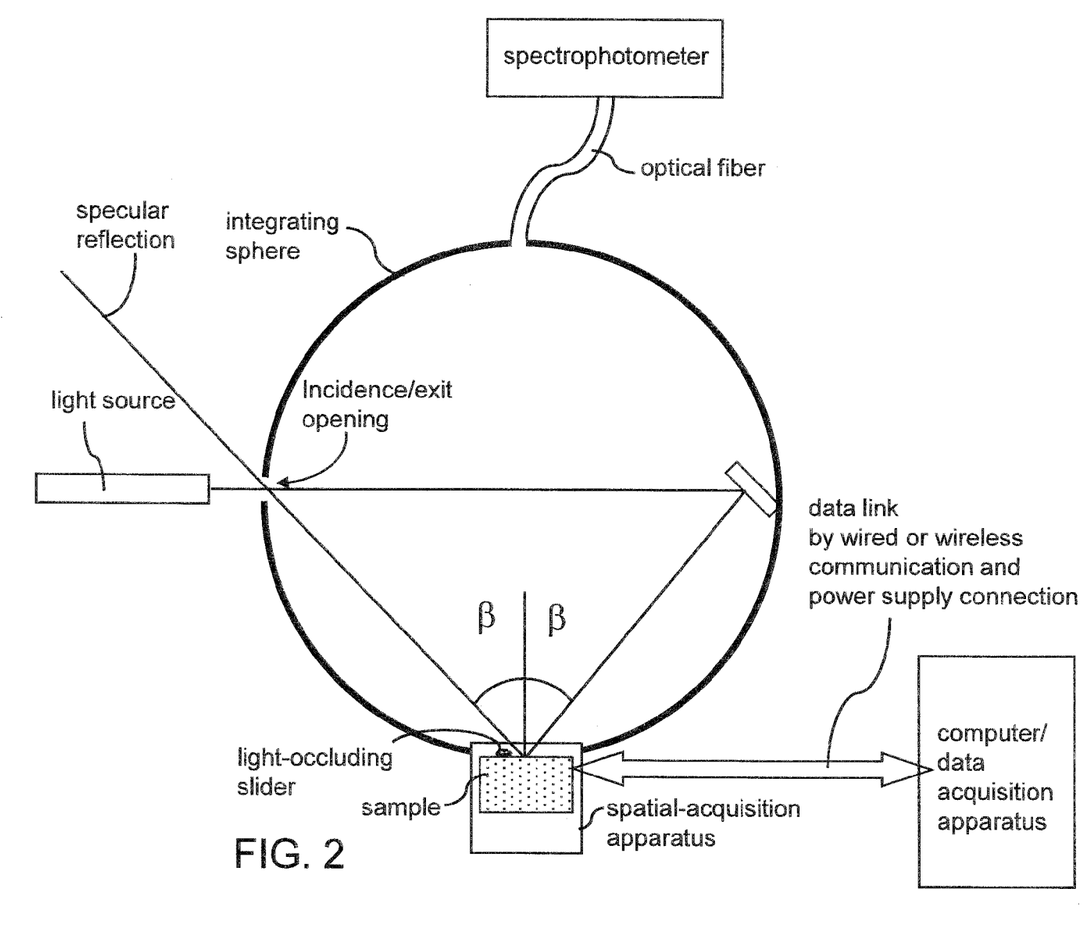
FIG. 2 is a schematic horizontal cross-sectional view of a second exemplary optical apparatus including a spatial-acquisition apparatus located on an optical integrating sphere and a spectrophotometer of the present invention.

Referring to FIGS. 1 and 2, a first exemplary optical apparatus and a second exemplary optical apparatus are shown, respectively, in a horizontal cross-sectional view. Each of the first and second exemplary optical apparatus includes an enclosure having a reflective inner surface, a spatial-acquisition apparatus configured to hold a sample on a front side, a light source, a light-occluding slider, a spectrophotometer, a linear motion controller (not shown in FIG. 1 or 2), a computer, a data acquisition apparatus, and peripheral devices configured to provide data link by wired or wireless communication and an optional power supply connection.

The first exemplary optical apparatus of FIG. 1 employs a center-mount configuration in which the spatial-acquisition apparatus and the sample are contained within the enclosure. This configuration allows for variable angle measurements in addition to the spatial measurements. In the first exemplary optical apparatus, the spatial-acquisition apparatus is located within the enclosure and has reflecting outer surfaces except on the front side. The front side of the spatial-acquisition apparatus is configured to pass the collimated incident light beam into the sample, and to pass the diffuse scattered light and a specular reflection beam of the incident light beam out of the sample. The enclosure includes a first aperture, which is an entry aperture for an illumination beam that is configured to pass the collimated incident light beam into the enclosure. The enclosure further includes a second aperture, which is an exit aperture for a specular reflection beam from a sample inside that is configured to pass the specular reflection beam of the incident light beam from the sample out of the enclosure. The enclosure may have a plurality of components that move relative to one another to alter the relative position between the first aperture and the second aperture.

The second exemplary optical apparatus of FIG. 2 employs a wall-mount configuration in which the spatial-acquisition apparatus is located just outside one of the side ports of the enclosure. This configuration provides a simpler means to insert and remove the sample, additionally providing an increased signal-to-noise ratio (SNR) since the sample does not interfere with equilibrium of light intensity within the integrating sphere. In the second exemplary optical apparatus, an angled mirror located near the rear port is necessary to direct the incoming light source towards the sample at an oblique angle of incidence. Outer walls of the spatial-acquisition apparatus are located outside the enclosure except on the front side. The front side of the spatial-acquisition apparatus is configured to pass the collimated incident light beam into the sample, and to pass a specular reflection beam of the incident light beam from the sample. The enclosure has an aperture configured to pass the collimated incident light beam into the enclosure and to pass a specular reflection beam of the incident light beam from the sample out of the enclosure. In this case, the aperture functions as an entry aperture for the illumination beam and an exit aperture for the specular reflection beam. A mirror within the enclosure may rotate and/or move to alter the beam path within the enclosure.

In the first and second exemplary optical apparatuses, the enclosure has an enclosed volume except for openings for letting light beams and a connection to the spectrophotometer. The inside surface of the enclosure comprises an optically reflective material or is coated with an optically reflective material. Preferably, the reflective inner surface of the enclosure extends across the entire inner surface of the enclosure. Preferably, the enclosure has a shape that facilitates reflection of light into an opening connected to the spectrophotometer. The enclosure can be an optical integrating sphere having a substantially spherical inner surface. Physical dimensions, such as length, width, and height, of the enclosure can be from 1 cm to 3 m, and typically are from 3 cm to 1 m, although lesser and greater dimensions are also contemplated herein. In case the enclosure is spherical in shape, the diameter of the enclosure can be from 1 cm to 3 m, and typically from 3 cm to 1 m, although lesser and greater dimensions are also contemplated herein. The first and second apertures in the first exemplary optical apparatus or the aperture in the second exemplary optical apparatus can have a lateral dimension, which is typically the diameter of each aperture, from 5 micron to 1 cm, and typically from 30 micron 300 micron, although lesser and greater dimensions are also contemplated herein.

The light source is configured to illuminate a collimated incident light beam onto a front surface of the sample. The collimated incident light beam can be a monochromatic light or can include a continuous spectrum of a wavelength range. The collimated light beam can be in the infrared range, the visible spectrum, the ultraviolet range, or a combination thereof. The size of the beam, as measured by lateral dimensions such as the diameter, can be from 1 micron to 500 microns, and typically from 3 microns to 100 microns, although lesser and greater lateral dimensions of the beam are also contemplated herein.

The sample is mounted to the front side of the spatial-acquisition apparatus. The sample can be any sample having optical characteristics, and can be a biological sample or a non-biological sample. In one embodiment, the sample can be a biological tissue or a material to replace a biological tissue. The sample is thick enough to allow full absorption of the collimated incident light beam so that the incident light beam does not penetrate the sample. The lateral dimensions of the sample are greater than the diameter of the collimated incident light beam preferably by at least one order of magnitude. Typically, the lateral dimensions of the sample can be from 10 microns to 1 m, and typically from 100 microns to 10 cm, although lesser and greater lateral dimensions of the sample are also contemplated herein.

The collimated incident light beam impinges on the front surface of the sample and produces a specular reflection beam and diffuse scattered light. The specular reflection beam comes from the sample at an angle having the same magnitude as the angle of incidence of the collimated incident light beam but having the opposite direction. The specular reflection beam is in the plane formed by the collimated incident light beam and the surface normal of the sample. The specular reflection beam is allowed to escape from the enclosure through an exit opening so that only the diffuse scattered light can be measured by the spectrometer. In the first exemplary optical apparatus, the incidence angle is represented by the angle $\alpha$. In the second exemplary optical apparatus, the incidence angle is represented by the angle $\beta$. Each of $\alpha$ and $\beta$ may vary from 0 degree to 90 degrees and typically range from 10 degree to 60 degrees. The relative position of the first and second aperture in the first exemplary optical apparatus may be altered as the angle $\alpha$ is varied to ensure that the specular reflection beam exits through the second aperture.

The mirror within the second exemplary optical apparatus may move or rotate to ensure that specular reflection beam exits through the aperture.

The diffuse scattered light is scattered in all directions available for emission from the front surface of the sample, i.e., in the direction of a hemisphere to the front side of the sample. The portion of the diffuse scattered light that happens to have the same direction of emission as the specular reflection beam exits the enclosure. This portion is a negligible portion, e.g., less than 1% and preferably less than 0.3%, of the total diffuse scattered light, because the spherical angle of the exit aperture is small compared to the spherical angle of the hemisphere available across which the direction of the diffuse scattered light is distributed. The spherical angle at the exit aperture, as measured by the lateral dimension such as the diameter of the exit aperture, is typically less than 0.03 radians, and preferably less than 0.01 radians, and more preferably less than 0.005 radians.

A light-occluding slider is configured to be able to cover a portion of the front side of the spatial-acquisition apparatus and configured to slide over the front side of the spatial-acquisition apparatus. Thus, a portion of the front surface of the sample can be covered by the light-occluding slider, while the remaining portions of the front surface of the sample are exposed for emission of the diffuse scattered light. Not necessarily but typically, the light-occluding slider is configured to slide out as needed to one side of the sample to allow full emission of diffuse scattered light without blocking.

When the light-occluding slider is positioned in front of the sample, the diffuse scattered light is divided into two portions. The portion the diffuse scattered light that is directed toward the area of the light-occluding slider is blocked by the light-occluding slider. The remaining portions of the diffuse scattered light is emitted without blockage by the light-occluding slider, reflected off the inner surface of the enclosure, and are eventually detected by the spectrometer minus a small amount that leaks out the specular reflection port, i.e. the less than 1%.

The spectrophotometer measures the intensity of incoming light as a function of the spectral wavelength. The spectrophotometer can be attached directly to the surface of the enclosure, or can be connected to the inside of the enclosure via an optical fiber. Any type of spectrophotometer can be employed for the purposes of the present invention including time-resolved spectrophotometers.

Figure 3:
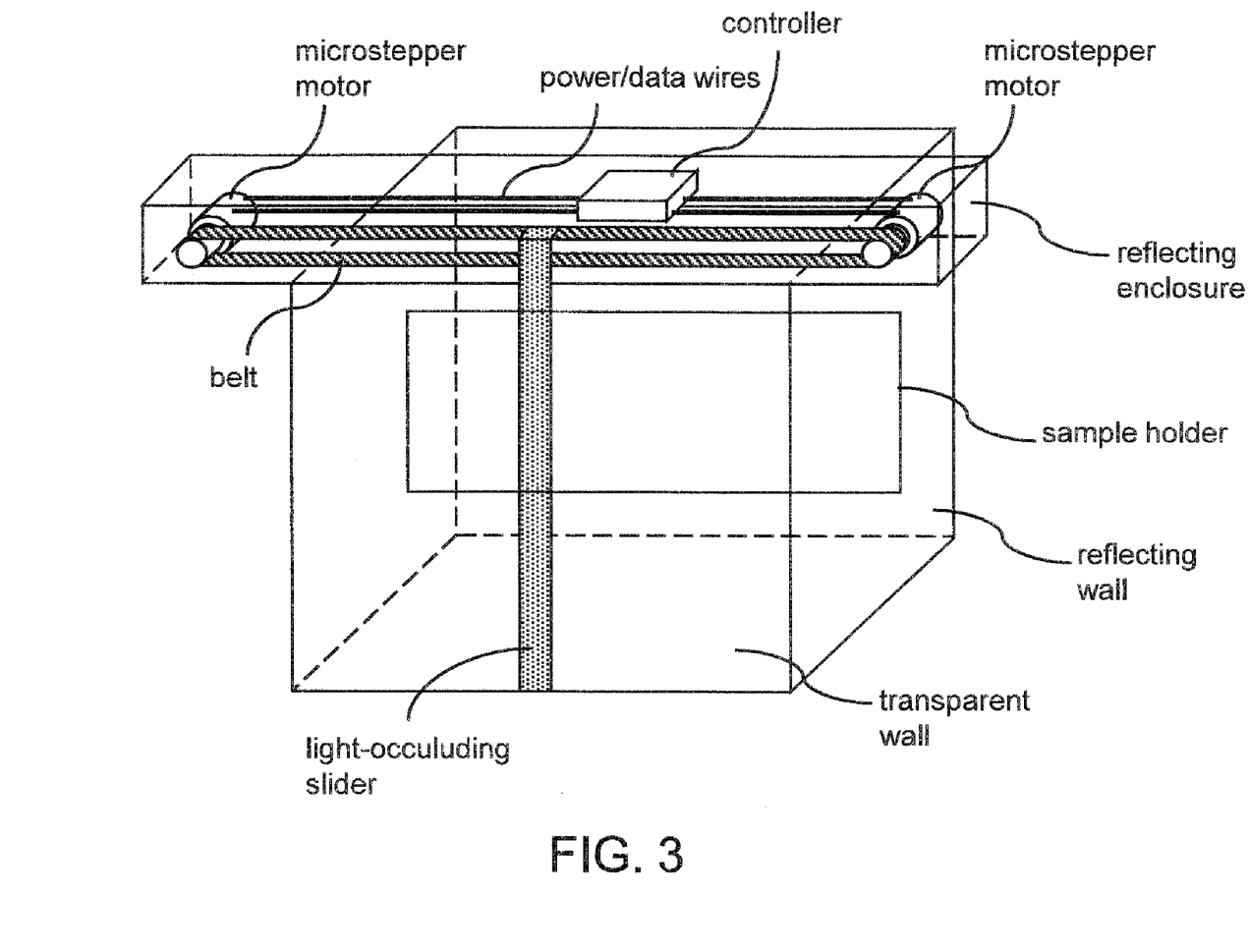
FIG. 3 is a see-through view of the spatial-acquisition apparatus of the present invention.

Referring to FIG. 3, the spatial-acquisition apparatus of the present invention is shown in detail. The spatial-acquisition apparatus includes a sample holder, spatial-acquisition apparatus walls, a light-occluding slider, at least one linear actuator, a controller, and peripheral components to enable control and movement of the at least one linear actuator. For example, the peripheral components can include a digital-to-analog converter and a power supply source.

The spatial-acquisition apparatus walls include reflecting or absorbing walls on the back side, the left side, and the right side. The spatial-acquisition apparatus walls can optionally include a transparent wall, such as a glass window, on the front side of the sample. In the case of the internal center-mount embodiment illustrated by the first exemplary optical apparatus in FIG. 1, all exposed surfaces of the spatial-acquisition apparatus walls except on the front side comprise, or are painted with, highly diffusely reflective material such as white barium sulfate to minimize absorption of diffuse scattered light by the apparatus. The sample holder is located within the spatial-acquisition apparatus walls.

The at least one linear actuator is configured to move linearly. For example, the at least one linear actuator can include a chain, a belt, a linear moving rack having teeth, or any other mechanical component configured to make a linear movement. Preferably, the direction of the movement of the at least one linear actuator is the direction formed by the intersection of a plane formed by the collimated incident light beam and the specular reflection beam and the plane of the front surface of the spatial-acquisition apparatus. At least one motor can be provided to trigger a linear motion of the at least one linear actuator. The at least one linear actuator and the at least one motor are placed within a reflecting or absorbing enclosure having reflective or absorbing outer surfaces.

The light-occluding slider is attached to, and moves with, the at least one linear actuator. The light-occluding slider covers a portion of the frontal area of the spatial-acquisition apparatus. The light-occluding slider can have any shape, and typically has the shape of a rectangular strip, i.e., a strip having a rectangular area with a hemispherical front surface as seen from the front side of the spatial-acquisition apparatus.

The controller is a linear motion controller that controls the linear motion of the light-occluding slider. The controller is configured to control movement of the at least one linear actuator and the light-occluding slider can be embedded within the reflecting enclosure. Power wires and data wires can be provided between the controller and actuation mechanisms for the at least one linear actuator, which can be micro-stepper motors. A digital-to-analog converter can also be provided so that the information on the directed or measured location of the light-occluding slider can be converted to digital format.

Figure 4:
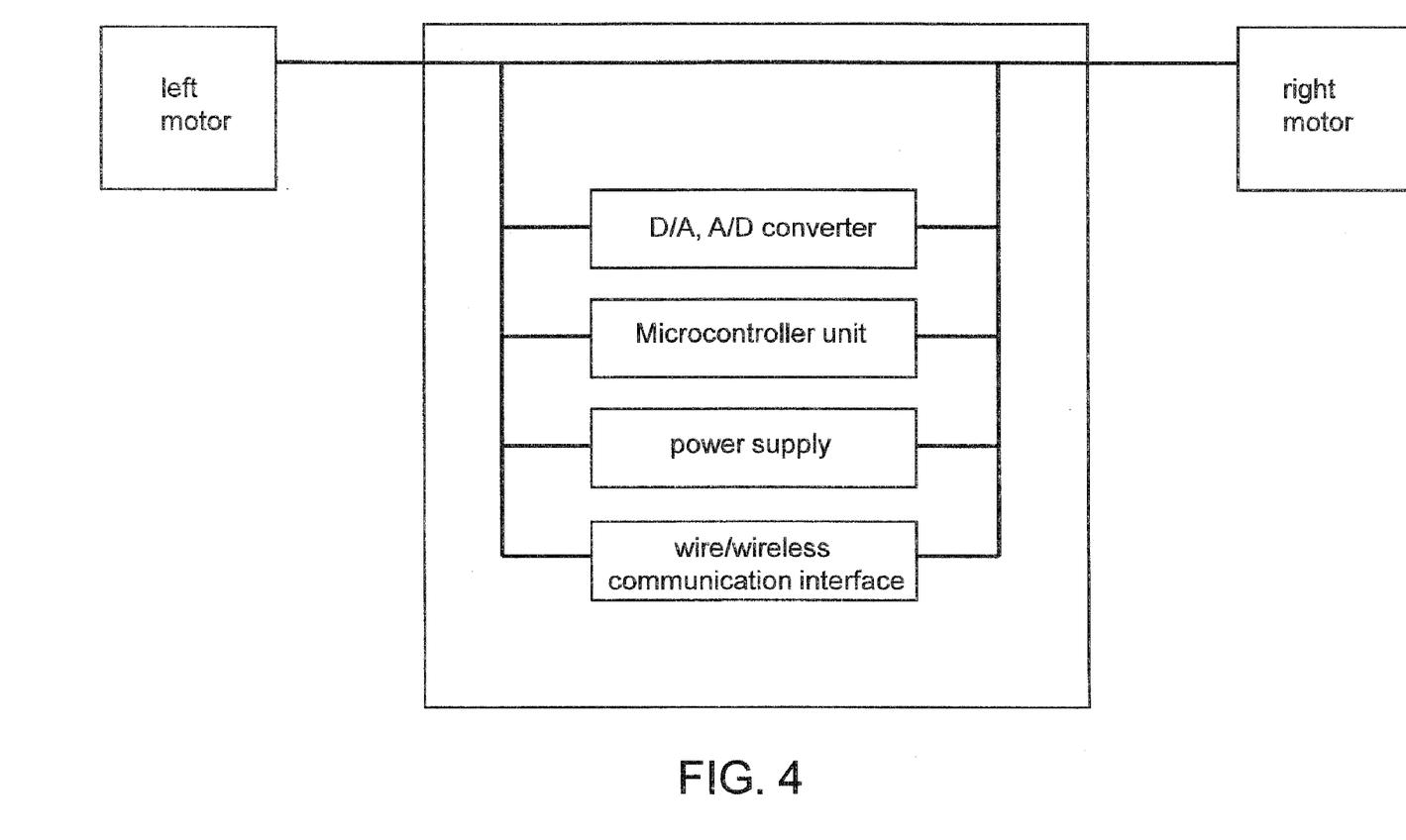
FIG. 4 is a schematic diagram of components of a controller of the present invention.

Referring to FIG. 4, the controller of the present invention includes a microcontroller unit and can include other components such as a power supply, a digital-to-analog (D/A) and/or analog-to-digital (A/D) converter, and wire/wireless communication interface. The power supply can include a power source or can include a cable connection to an external power supply unit located outside the enclosure. The D/A and/or A/D converter convert information on the location of the at least one liner actuator into digital format. Further, the D/A and/or A/D converter can be employed to provide an analog signal to at least one motor (such as the left motor and the right motor) based on the digital signal from the microcontroller unit.

Figure 5:
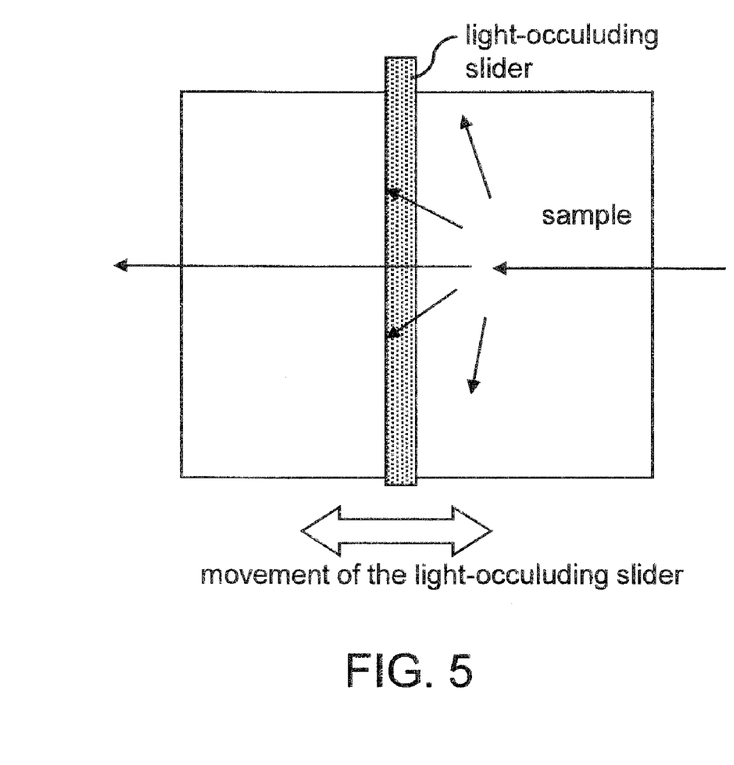
FIG. 5 is a front view of the spatial-acquisition apparatus without showing the linear motion controller according to the present invention.
Figure 6:
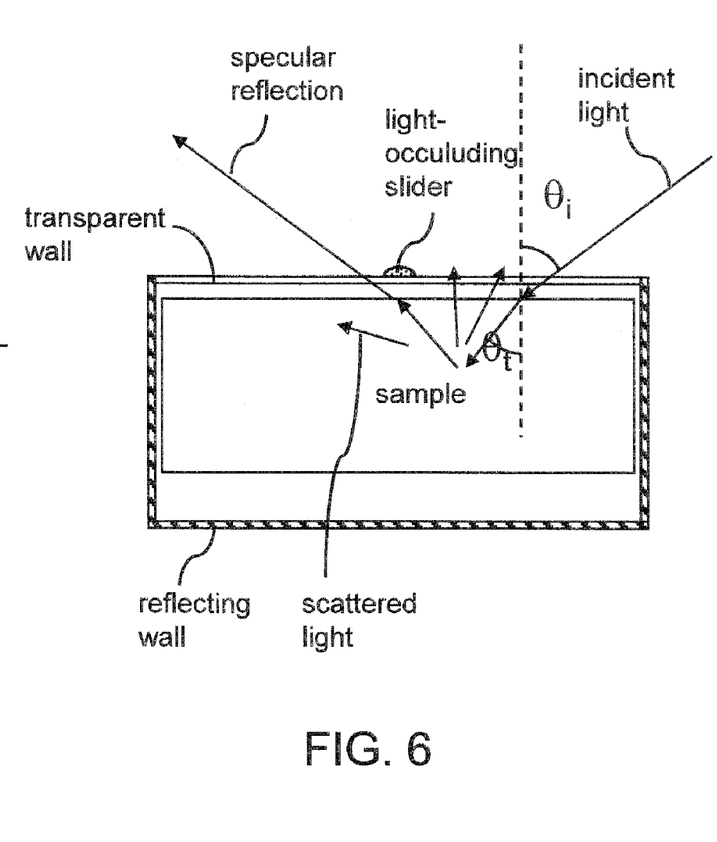
FIG. 6 is a horizontal cross-sectional view of the spatial-acquisition apparatus of the present invention.

Referring to FIGS. 5 and 6, operation of the optical apparatus of the present invention is illustrated by a frontal view and a horizontal cross-sectional view, respectively, of the spatial-acquisition apparatus of the present invention.

As discussed above, the prior art does not provide any way of determining spatial data within an integrating sphere. In contrast, the present invention provides a novel method for extracting the intensity distribution of the diffuse scattered light over the surface of a sample. This extraction is effected via the use of a light-occlusion device, i.e., the light occluding slider (LOS). As the light-occluding slider is positioned at a certain point along the sample's surface, the contribution of diffuse reflectance from this particular position is blocked. The measured signal at the spectrophotometer is the sum of diffuse reflectance at every other area except the area covered by the light-occluding slider.

During the operation of the optical apparatus of the present invention, a sample is loaded on a front side of the spatial-acquisition apparatus. Typically, the sample is loaded onto a sample holder in the spatial-acquisition apparatus such that the front surface of the sample is exposed on the front side of the spatial-acquisition apparatus. After moving the light-occluding slider to a desired position, which can be a position located over the front surface of the sample or a position that does not block the front side of the sample, the collimated incident light beam is illuminated onto the front surface of the sample. If the light-occluding slider is located over the front surface of the sample, the light-occluding slider blocks a portion of diffuse scattered light from the sample that is emitted upon irradiation of the sample with the collimated incident light. The unblocked portion of the diffuse scattered light is detected employing the spectrophotometer attached to the inside of the enclosure for each location of the light-occluding slider. If the light-occluding slider is located such that the front surface of the sample is not blocked by the light-occluding slider, all the diffuse scattered light from the front surface of the sample is collected and measured at the spectrophotometer (except for the inherent built-in loss during reflection of light inside the enclosure).

To determine the diffuse reflectance of an area covered by the light-occluding slider, the total baseline diffuse reflectance is first measured by moving the light occluding slider out of the area of the exposed area of the sample and illuminating the sample with the incident light beam. The light-occluding slider is then placed over the area, thereby blocking and absorbing the diffuse reflection from the area of the sample directly underneath, and the spectrophotometer measures the diffuse reflectance from the exposed area of the sample as the incident light beam illuminates the sample. The measured diffuse reflectance with a light-occluding slider over a predetermined area of the sample is subtracted from the total baseline diffuse reflectance to obtain the diffuse reflectance from the area of the sample covered by the light-occluding slider.

The light-occluding slider has a back surface configured to face the sample. The back surface of the light-occluding slider is a light-absorbing surface, which can be implemented by a light-absorbing material or coating such as Derlin.

Preferably, the distance between the back side of the light-occluding slider and the front surface of the sample is minimized. In one embodiment, the light-occluding slider contacts the front surface of the sample. In another embodiment, the light-occluding slider is separated from the front surface of the sample by an infinitesimal distance. In yet another embodiment, the light-occluding slider is separated from the front surface of the sample by a constant predetermined distance. In still another embodiment, the light-occluding slider is separated from the front surface of the sample by a transparent barrier wall such as a glass window. In this case, the transparent barrier wall is configured to cover the sample, to pass the collimated incident light beam into the sample, and to pass the diffuse scattered light and the specular reflection beam of the incident light beam out of the sample, while preventing the transfer of material across the transparent barrier wall. The transparent barrier wall can be advantageously employed to prevent contamination of the inner reflective surface of the enclosure by accidental discharge of any material from the sample such as, for example, oozing liquid from a biological sample.

The refractive index of the medium outside the sample (which is typically air or inert gas) is herein referred to as $\eta_i$, and the refractive index of the sample is herein referred to as $\eta_t$. During measurements of the intensity of the diffuse scattered light by the spectrophotometer, the collimated incident light beam impinges on the sample with an oblique incidence angle, $\theta_i$, and is refracted at an angle, $\theta_t$, due to the mismatch between the refractive indices $\eta_i$ and $\eta_t$. Once inside the tissue sample, the light is scattered. For a sufficiently thick sample, this process is well characterized by the analytical diffusion theory model and the tissue optical properties can be determined as follows.

Tissue scatter has the effect of shifting the center of the re-emitted diffuse reflectance by an amount, $\Delta x$, given by:

$$\Delta x = \frac{\sin(\theta_t)}{\mu'_s + 0.35\mu_a}, \tag{1}$$

where $$\theta_t = \sin^{-1}\left(\frac{\eta_i}{\eta_t} \cdot \sin(\theta_i)\right). \tag{2}$$

Essentially, tissue scatter creates a shifted location embedded source remittance profile, with the amount of shift determined by sample optical properties. For a sufficiently thick sample, from diffusion theory the value of the diffusion coefficient can be obtained via $$D = \frac{\Delta x}{3 \cdot \sin(\theta_t)} = \frac{1}{3(\mu'_s + 0.35\mu_a)} \tag{3}$$

The measured diffuse reflectance as a function of position, x, from the point of oblique light incidence can be determined by:

$$R_d(x) = \left(\frac{1 - a' \cdot R_{sp}}{4\pi}\right) \cdot \left(\frac{z'_s \cdot (1 + \mu_{eff} \cdot \rho_1) \cdot e^{-\mu_{eff} \cdot \rho_1}}{\rho_1^3} + \frac{(z'_s + 2z_b) \cdot (1 + \mu_{eff} \cdot \rho_2) \cdot e^{-\mu_{eff} \cdot \rho_2}}{\rho_2^3}\right). \tag{4}$$

where $R_{sp}$ is specular reflectance, a' is the transport albedo, $z'_s$, is the depth of the embedded normal incidence point source, $\mu_{eff}$, is the effective attenuation coefficient, $\rho_1$ and $\rho_2$ are the distances of the normal incidence and embedded image source respectively from the occluded point on the sample surface, for which the diffusive reflectance is being measured.

$$\mu_{eff} = \sqrt{\mu_a/D}. \tag{5}$$

The absorption coefficient can be computed by combing Eqns. 4 and 5 to yield:

$$\mu_a = D \cdot \mu_{eff}^2, \tag{6}$$

And the reduced scattering coefficient by, $$\mu'_s = \frac{1}{3D} - 0.35\mu_a. \tag{7}$$

Ideally the light-occluding slider would be a light sink on the tissue side, i.e. totally absorb all incident light, and a diffuse reflector on the side facing the light source. To minimize specular reflection effects on the light source side, it can be coated with $BaSO_4$, the integrating sphere diffusing coating material, to prevent/minimize specular reflection errors for the measurements. The tissue side of the light-occluding slider would be colored black so as to absorb all remitted light incident on the light-occluding slider for all wavelengths and the surface can be diffused (frosted) instead of smoothed to prevent/minimize specular reflection back into the tissue which would contribute measurement error. Using a black diffuser on the tissue side of the light-occluding slider, enables and/or facilitates multi-spectral optical properties determination.

The at least one linear actuator can be linearly moved by a signal from the controller such that the at least one linear actuator moves with the light-occluding slider. The unblocked portion of the diffuse scattered light can be detected for a plurality of locations of the light-occluding slider as the light-occluding slider is moved.

The optical apparatus can include a data acquisition apparatus to automate the data acquisition for at least one location, and preferably at a plurality of locations, of the light-occluding slider. The data acquisition apparatus acquires two types of data. The first data describes a location of the light-occluding slider and the second data describes measured intensity of the unblocked portion of the diffuse scattered light as measured by the spectrometer when the light-occluding slider is at that location. The data acquisition apparatus can be configured to record at least one pair of first data and second data, and preferably a plurality of pairs of the first data and the second data.

The movement of the light-occluding slider can be controlled by a computer. In this case, any computer software to provide a control interface for manipulating the movement of the at least one linear, for coordinating the collection of reflectance intensity data from the spectrophotometer, and for converting the collected intensity data into the optical properties of the sample. Any computer language such as C, C++, LabVIEW™, and MATLAB™ may be employed to program computer software for this purpose.

Further, the computer can be configured to receive data from the data acquisition apparatus and to record a plurality of pairs of the first data and the second data corresponding to different locations of the light-occluding slider during a linear movement. The computer can be configured to calculate diffuse reflectance for each area blocked by the light-occluding slider based on the plurality of pairs of the first data and the second data. Such automatic data collection with the movement of the light-occluding slider for each corresponding location of the light-occluding slider can be effected by running a self-executing program that causes a linear movement of the light-occluding slider and triggers a measurement by the spectrophotometer.

Diffuse reflectance can be calculated for each area blocked by the light-occluding slider based on the plurality of pairs of the first data and the second data and the total baseline diffuse reflectance data. Further, the absorption coefficient and the scattering coefficient of the sample can be calculated based on the diffuse reflectance for each area blocked by the light-occluding slider.

The program that automatically executes data collection with the movement of the light-occluding slide can be stored in a machine-readable data storage device such as a computer hard disk, a portable memory device, a compact disk (CD), a digital video disk (DVD), a tape drive, or any other electronic data storage device. The machine-readable data storage device may be a portable memory device that is readable by a computer, or may be a built-in component of a computer such as a semiconductor memory chip, a memory chiplet embedded in a semiconductor microprocessor, or a hard disk. Such program includes machine-executable instructions in a machine-readable format to operate the optical apparatus of the present invention. Upon execution on the computer, the program of machine-executable instructions can cause a linear movement of the light-occluding slider and trigger a measurement by the spectrophotometer and further cause the plurality of pairs of the first data and the second data to be automatically collected for each corresponding location of the light-occluding slider.

In case the computer is configured to receive data from the data acquisition apparatus and to record a plurality of pairs of the first data and the second data corresponding to different locations of the light-occluding slider during a linear movement, the computer can be operated using the program to automate the measurement of the present invention. Further, the program can include instructions for calculating diffuse reflectance for each area blocked by the light-occluding slider based on the plurality of pairs of the first data and the second data. In addition, the program can also include instructions for calculating the absorption coefficient and the scattering coefficient of the sample based on the diffuse reflectance for each area blocked by the light-occluding slider.

Figure 7:
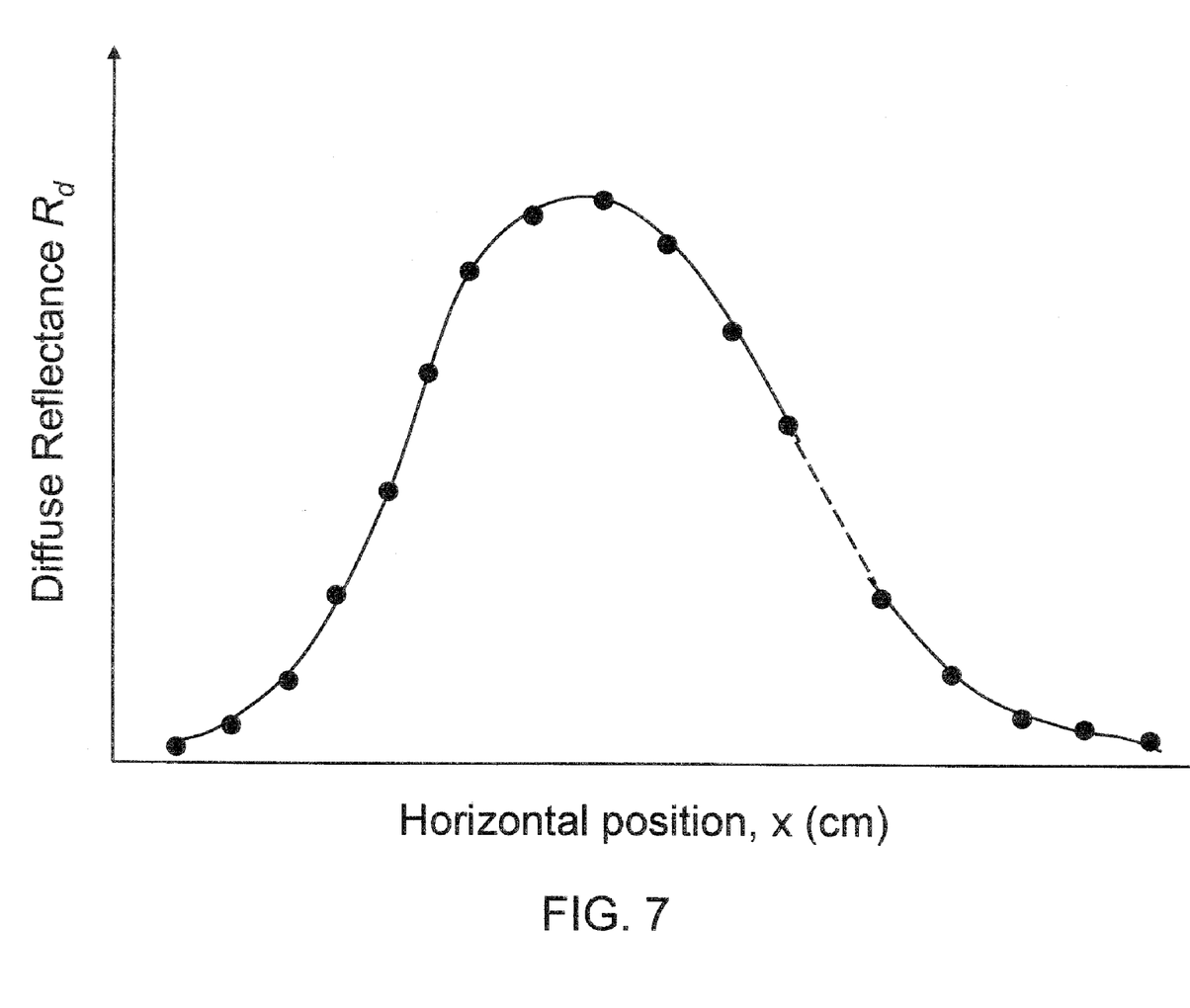
FIG. 7 is a plot of diffuse reflectance as a function of the horizontal position of a light-occluding slider.

Referring to FIG. 7, a plot of diffuse reflectance is shown as a function of the horizontal position of a light-occluding slider. The dark circles represent calculated data values for diffuse reflectance of the area of the sample corresponding to the locations measured with the light-occluding slider positioning. The solid lines represent a fitted curve. The missing data point and the dotted line represent the location of the light-occluding slider when the light-occluding slider intercepts the collimated incident light beam. The diffuse reflectance curve thus derived is fitted with parametrized theoretical curves to determine the parameters of the model, i.e., the scatter and absorption coefficients as a function of direction relative to the incident light beam.

Spatial information of diffuse scattered light can be extremely useful in a variety of applications, including the determination of optical properties from biological tissue or any application where a heterogeneous spatially varying sample is under investigation. In the prior art, the inherent nature of an integrating sphere limits the acquisition of spatial information. The present invention addresses this limitation while still reaping the benefits of the standard integrating-sphere by providing a compatible "add-on" accessory to re-incorporate spatial information into an integrating sphere, for use in a plethora of important applications ranging from bio-medical optics to non-destructive testing in agriculture.

In contrast to the prior art methods that require movement of the sample during multiple measurements, the present invention provides a completely automated system, which requires no sample movement for measurement, and thereby eliminating degrees of freedom from the measurement process to produce more consistent measurements. In addition, implementation of the present invention is cost-effective, as it does not require a second integrating sphere to be purchased.

In addition, the prior art method for determining optical properties is dependent on extremely thin samples for both the single and double integrating sphere approaches as discussed above. A rather expensive process is involved which requires the purchase of a microtome to precisely cut the sample into thin slices. Aside from the high cost, this method requires first freezing the sample, thus changing its physical properties. The change in physical properties corresponds to a change in the optical properties of the sample, resulting in systematically inaccurate measurements. In addition to this, the requirement to slice the tissue leads to a destructed sample, so this method can only be used on disposable samples. The present invention provides a low-cost, accurate method of collecting data from thicker samples, bypassing the need to purchase a microtome, freeze the sample, or cause any structural damage to the tissue because it is non sample destructive.

The present invention enables instantaneous multi-spectral measurement of optical properties, with a wavelength range determined by the frequency bandwidths of both the input light source and fiber optically coupled spectrophotometer detector. This obviates the typical time consuming process of serial multi-spectral optical properties determination. Additionally, the shorter sample data collection time enables preservation of sample "freshness."

There are a multitude of areas within industry that can derive significant benefit from the disclosed invention. For example, one of the largest growing research areas within the biomedical industry involves tissue engineering and bioartificial constructs. It is vital to constantly integrate functional and structural testing into the development process to guide the development and routinely evaluate the efficacy of the construct. One key marker of structure is the reduced scattering and absorption coefficients (optical properties) of the sample. As such, as the field of tissue engineering grows, the need for accurate validation tools (such as the disclosed invention) is accordingly expanding.

In addition to tissue engineering development, fields that involve any sort of surgical tissue insertion would benefit. For instance, transplantable organs and porcine heart valves require an extensive sterilization process, whereby there exists a possibility to deleteriously modify the tissue. Incorrectly processed tissues have been known to cause medical complications. Thus, it is imperative to thoroughly assess these tissues before clinical use. A prominent marker for structural integrity is the optical properties of the tissue sample.

Many biomedical research or clinical technology that uses a laser to interact with biological tissue relies on optical properties as a basis for assessing how light will travel through tissue or for understanding physical changes within tissue. The disclosed invention can be extremely useful in applications stemming from the development of clinical diagnostics, clinical therapeutics, to any biomedical research application where structural assessment of tissue is necessary.

The present invention is a valuable addition to optical systems that employ integrating spheres. In addition, many other applications of the present invention are possible both in the biomedical field and outside the biomedical field.

While the invention has been described in terms of specific embodiments, it is evident in view of the foregoing description that numerous alternatives, modifications and variations will be apparent to those skilled in the art. Other suitable modifications and adaptations of a variety of conditions and parameters normally encountered in molecular biology, protein chemistry, and protein modeling, obvious to those skilled in the art, are within the scope of this invention. All publications, patents, and patent applications cited herein are incorporated by reference in their entirety for all purposes to the same extent as if each individual publication, patent, or patent application were specifically and individually indicated to be so incorporated by reference. Accordingly, the invention is intended to encompass all such alternatives, modifications and variations which fall within the scope and spirit of the invention and the following claims.

What is claimed is:

1. An optical apparatus comprising:
   an enclosure having a reflective inner surface;
   a spatial-acquisition apparatus configured to hold a sample on a front side, wherein said front side is exposed to an interior of said enclosure;
   a light source configured to illuminate a collimated incident light beam onto a front surface of said sample; and
   a light-occluding slider covering a portion of said front side of said spatial-acquisition apparatus and configured to slide over said front side of said spatial-acquisition apparatus, wherein said light-occluding slider blocks a portion of diffuse scattered light from said sample upon irradiation with said collimated incident light.

2. The optical apparatus of claim 1, further comprising a spectrophotometer configured to detect an unblocked portion of said diffuse scattered light, and wherein said reflective inner surface extends across an entire inner surface of said enclosure.

3. The optical apparatus of claim 2, wherein said enclosure is an optical integrating sphere having a substantially spherical inner surface.

4. The optical apparatus of claim 2, further comprising at least one linear actuator that is configured to move linearly, wherein said light-occluding slide is attached to said at least one linear actuator.

5. The optical apparatus of claim 4, further comprising at least one motor that is configured to trigger a linear motion of said at least one linear actuator.

6. The optical apparatus of claim 4, further comprising a controller configured to control movement of said at least one linear actuator and said light-occluding slider.

7. The optical apparatus of claim 6, further comprising a data acquisition apparatus configured to record at least one pair of first data and second data, wherein said first data describes a location of said light-occluding slider and said second data describes measured intensity of said unblocked portion of said diffuse scattered light as measured by said spectrometer when said light-occluding slider is at said location.

8. The optical apparatus of claim 7, further comprising a computer configured to receive data from said data acquisition apparatus and to record a plurality of pairs of said first data and said second data corresponding to different locations of said light-occluding slider during a linear movement.

9. The optical apparatus of claim 8, wherein said computer is configured to calculate diffuse reflectance for each area blocked by said light-occluding slider based on said plurality of pairs of said first data and said second data.

10. The optical apparatus of claim 2, wherein said light-occluding slider has a back surface configured to face said sample, wherein said back surface is a light-absorbing surface.

11. The optical apparatus of claim 2, wherein said spatial-acquisition apparatus is located within said enclosure and has reflecting outer surfaces except on said front side, wherein said front side is configured to pass said collimated incident light beam into said sample, and to pass said diffuse scattered light and a specular reflection beam of said incident light beam out of said sample.

12. The optical apparatus of claim 11, further comprising:
   a first aperture located on said enclosure and configured to pass said collimated incident light beam into said enclosure; and
   a second aperture located on said enclosure and configured to pass a specular reflection beam of said incident light beam from said sample out of said enclosure.

13. The optical apparatus of claim 2, wherein outer walls of said spatial-acquisition apparatus are located outside said enclosure except on said front side, wherein said front side is configured to pass said collimated incident light beam into said sample, and to pass said diffuse scattered light and a specular reflection beam of said incident light beam out of said sample.

14. The optical apparatus of claim 13, further comprising an aperture located on said enclosure configured to pass said collimated incident light beam into said enclosure and to pass a specular reflection beam of said incident light beam from said sample out of said enclosure.

15. The optical apparatus of claim 2, wherein said spatial-acquisition apparatus includes a transparent barrier wall configured to cover said sample, to pass said collimated incident light beam into said sample, to pass said diffuse scattered light and a specular reflection beam of said incident light beam out of said sample, and to prevent transfer of material across said transparent barrier wall.

16. A method of operating an optical apparatus comprising:
providing an optical apparatus including an enclosure having a reflective inner surface and a spatial-acquisition apparatus;
loading a sample on a front side of said spatial-acquisition apparatus;
illuminating a collimated incident light beam onto a front surface of said sample;
moving a light-occluding slider over said front surface of said sample, wherein said light-occluding slider blocks a portion of diffuse scattered light from said sample upon irradiation with said collimated incident light; and
detecting an unblocked portion of said diffuse scattered light employing a spectrophotometer attached to an inside of said enclosure for at least one location of said light-occluding slider.

17. The method of claim 16, wherein said unblocked portion of said diffuse scattered light is detected for a plurality of locations of said light-occluding slider.

18. The method of claim 16, wherein said enclosure is an optical integrating sphere having a substantially spherical inner surface.

19. The method of claim 16, further comprising linearly moving at least one linear actuator by a signal from a controller, wherein said at least one linear actuator moves with said light-occluding slider.

20. The method of claim 16, further comprising collecting at least one pair of first data and second data employing a data acquisition apparatus, wherein said first data describes a location of said light-occluding slider and said second data describes measured intensity of said unblocked portion of said diffuse scattered light as measured by said spectrometer when said light-occluding slider is at said location.

21. The method of claim 20, further comprising operating a computer configured to receive data from said data acquisition apparatus and to record a plurality of pairs of said first data and said second data corresponding to different locations of said light-occluding slider during a linear movement.

22. The method of claim 21, further comprising calculating diffuse reflectance for each area blocked by said light-occluding slider based on said plurality of pairs of said first data and said second data.

23. The method of claim 22, further comprising calculating an absorption coefficient and a scattering coefficient of said sample based on said diffuse reflectance for each area blocked by said light-occluding slider.

24. The method of claim 21, wherein said plurality of pairs of said first data and said second data is collected automatically for each corresponding location of said light-occluding slider by running a self-executing program that causes a linear movement of said light-occluding slider and triggers a measurement by said spectrophotometer.

25. A machine-readable data storage device embodying a program of machine-executable instructions to perform a method of operating an optical apparatus,
wherein said optical apparatus comprises:
a spatial-acquisition apparatus configured to hold a sample on a front side;
a light source configured to illuminate a collimated incident light beam onto a front surface of said sample; and
a light-occluding slider covering a portion of said front side of said spatial-acquisition apparatus, wherein said light-occluding slider blocks a portion of diffuse scattered light from said sample upon irradiation with said collimated incident light,
and wherein said method comprises:
moving a light-occluding slider over a front surface of said sample while a collimated incident light beam is illuminated onto a front surface of said sample, wherein said light-occluding slider blocks a portion of diffuse scattered light from said sample upon irradiation with said collimated incident light; and
detecting an unblocked portion of said diffuse scattered light employing a spectrophotometer for at least one location of said light-occluding slider.

26. The machine-readable data storage device of claim 25, wherein said optical apparatus further comprises an enclosure having a reflective inner surface, wherein said front side of said spatial-acquisition apparatus is exposed to an interior of said enclosure.

27. The machine-readable data storage device of claim 26, wherein said enclosure is an optical integrating sphere having a substantially spherical inner surface.

28. The machine-readable data storage device of claim 25, wherein said method further comprises detecting said unblocked portion of said diffuse scattered light for a plurality of locations of said light-occluding slider.

29. The machine-readable data storage device of claim 25, wherein said method further comprises linearly moving at least one linear actuator by a signal from a controller, wherein said at least one linear actuator moves with said light-occluding slider.

30. The machine-readable data storage device of claim 25, wherein said method further comprises collecting at least one pair of first data and second data employing a data acquisition apparatus, wherein said first data describes a location of said light-occluding slider and said second data describes measured intensity of said unblocked portion of said diffuse scattered light as measured by said spectrometer when said light-occluding slider is at said location.

31. The machine-readable data storage device of claim 30, wherein said method further comprises operating a computer configured to receive data from said data acquisition apparatus and to record a plurality of pairs of said first data and said second data corresponding to different locations of said light-occluding slider during a linear movement.

32. The machine-readable data storage device of claim 31, wherein said method further comprises calculating diffuse reflectance for each area blocked by said light-occluding slider based on said plurality of pairs of said first data and said second data.

33. The machine-readable data storage device of claim 32, wherein said method further comprises calculating an absorption coefficient and a scattering coefficient of said sample based on said diffuse reflectance for each area blocked by said light-occluding slider.

34. The machine-readable data storage device of claim 31, wherein said program of machine-executable instructions causes a linear movement of said light-occluding slider and triggers a measurement by said spectrophotometer and further causes said plurality of pairs of said first data and said second data to be automatically collected for each corresponding location of said light-occluding slider.

35. The machine-readable data storage device of claim 31, wherein said machine-readable data storage device is a portable memory device that is readable by a computer.

36. The machine-readable storage device of claim 31, wherein said machine-readable data storage device is a built-in component of a computer.

* * * * *